United States Patent
Rubilar Fuentes et al.

(10) Patent No.: US 12,016,888 B2
(45) Date of Patent: Jun. 25, 2024

(54) PROCESS FOR OBTAINING BIOLOGICALLY ACTIVE COMPOSITIONS FROM EMU OIL, ANTI-INFLAMMATORY AND ANTI-IRRITANT PHARMACEUTICAL COMPOSITION, AND SKIN REGENERATIVE PHARMACEUTICAL COMPOSITION

(71) Applicants: NATURALIS S.A., Santiago (CL); PONTIFICIA UNIVERSIDAD CATOLICA DE VALPARAISO, Valparaíso (CL)

(72) Inventors: Macarena Cecilia Rubilar Fuentes, Santiago (CL); Carola Sofia Bahamondes Donoso, Casablanca (CL); Thomas Haack, Nunoa Santiago (CL); Maria Cecilia Branes Oshima, Vina del Mar (CL); Rolando Chamy Maggi, Curauma Valparaiso (CL)

(73) Assignees: NATURALIS S.A., Quilicura Santiago (CL); PONTIFICIA UNIVERSIDAD CATOLICA DE VALPARAISO, Valparaiso (CL)

( * ) Notice: Subject to any disclaimer, the term of this patent is extended or adjusted under 35 U.S.C. 154(b) by 453 days.

(21) Appl. No.: 17/604,541

(22) PCT Filed: May 4, 2020

(86) PCT No.: PCT/IB2020/054219
§ 371 (c)(1),
(2) Date: Oct. 18, 2021

(87) PCT Pub. No.: WO2020/225712
PCT Pub. Date: Nov. 12, 2020

(65) Prior Publication Data
US 2022/0193145 A1    Jun. 23, 2022

(30) Foreign Application Priority Data

May 6, 2019 (CL) .................................... 1240-2019

(51) Int. Cl.
*B01D 3/14* (2006.01)
*A61K 35/57* (2015.01)
(Continued)

(52) U.S. Cl.
CPC .............. *A61K 35/57* (2013.01); *A61K 47/10* (2013.01); *A61K 47/14* (2013.01); *A61K 47/183* (2013.01);
(Continued)

(58) Field of Classification Search
CPC ....................................................... B01D 3/14
See application file for complete search history.

(56) References Cited

U.S. PATENT DOCUMENTS 5,431,924 A     7/1995  Ghosh
5,677,338 A  * 10/1997  Manker .................. A01N 63/10
                                                     424/DIG. 10
(Continued)

FOREIGN PATENT DOCUMENTS

CN         1213311 A  *  4/1999  ............. A01N 37/06

OTHER PUBLICATIONS

International Search Report and Written Opinion for Corresponding International Application No. PCT/IB2020/054219, Jul. 28, 2020, 7 pages.

*Primary Examiner* — Rosanne Kosson
(74) *Attorney, Agent, or Firm* — LUCAS & MERCANTI, LLP

(57) ABSTRACT

A process for obtaining biologically active compositions from emu oil is provided, wherein the compositions are obtained by molecular distillation of the oil, both the dis-
(Continued)

tillate and the distillation residue being biologically active compositions. More specifically, a process for obtaining biologically active compositions from refined emu oil is disclosed, which has the following steps: (a) feeding emu oil at a flow of between 1 to 300 kg/h*m2 to a molecular distillation column at a pressure between 0.0001 mbar and 0.05 mbar and at an evaporator temperature between 160° C. and 250° C., for generating a distillate and a residue; and (b) collecting the distillate from the column, the distillate being a biologically active composition, and (c) collecting the residue from the column, the residue being a biologically active composition.

3 Claims, 2 Drawing Sheets

(51) Int. Cl.
*A61K 47/10* (2017.01)
*A61K 47/14* (2017.01)
*A61K 47/18* (2017.01)
*A61K 47/22* (2006.01)
*A61K 47/26* (2006.01)
*A61P 17/02* (2006.01)

(52) U.S. Cl.
CPC .............. *A61K 47/22* (2013.01); *A61K 47/26* (2013.01); *A61P 17/02* (2018.01)

(56) References Cited

U.S. PATENT DOCUMENTS

| | | |
|---|---|---|
| 5,958,384 A | 9/1999 | Holick |
| 2005/0123479 A1 | 6/2005 | Ferrante |
| 2009/0048338 A1 | 2/2009 | Turner |
| 2009/0068128 A1 | 3/2009 | Waddington |

* cited by examiner

PROCESS FOR OBTAINING BIOLOGICALLY ACTIVE COMPOSITIONS FROM EMU OIL, ANTI-INFLAMMATORY AND ANTI-IRRITANT PHARMACEUTICAL COMPOSITION, AND SKIN REGENERATIVE PHARMACEUTICAL COMPOSITION

CROSS REFERENCE TO RELATED APPLICATION

This Application is a 371 of PCT/IB2020/054219 filed on May 4, 2020, which claimed priority of Chilean Patent Application No. 1240-2019, filed May 6, 2019, both of which are incorporated herein by reference.

FIELD OF THE INVENTION

The present invention discloses a process for obtaining biologically active compositions from emu oil, said compositions are obtained by molecular distillation of the oil, both the distillate and the distillation residue being biologically active compositions.

STATE OF THE ART

The concrete technical problem is to obtain biologically active compositions from emu oil, where the biological activities of the obtained compositions are higher than the corresponding activities of emu oil. The process of the present invention is a solution to said technical problem.

The biological activity of emu oil, (*Dromaius novaehollandiae*), particularly its anti-inflammatory activity, is widely known. There is a vast scientific literature on the matter and numerous patents that disclose pharmaceutical compositions for treating both systemic inflammatory response syndrome and local inflammations caused by external agents.

Likewise, burn repairing activity of emu oil has been reported in various publications. For example, Gong, Z.-Y & Wang, J.-H & Qiu, X.-W & Li, Z.-Q & Yi, C.-H. (2005). "Effects of emu oil on tissue repair in wound healing of deep second degree burn in rats". Chinese Journal of Clinical Rehabilitation 9 (18): 119-121, Ghaderi, Prof. Dr. Reza. (2016). Effects of topical Emu oil on burn wounds in the skin of Balb/c mice. Dermatology Research and Practice, in press, M Penturf, PhD, R D S O'Banion, RPh J A Griswold, MD "Evaluation of Emu Oil in Lubrication and Treatment of Healed Burn Wounds" *The Journal of Burn Care & Rehabilitation*. Volume 19, Issue suppl_1_pt_2, 1 Jan. 1998, Pages S253. Pharmaceutical compositions containing emu oil have also been disclosed by U.S. Pat. No. 5,431,924, which additionally discloses an emu oil derived fraction, which is identified only as the "yellow fraction" having anti-inflammatory activity, and a chromatographic process to obtain said fraction, data of the in vivo anti-inflammatory activity of emu oil and the yellow fraction is provided in Tables 8 and 10, respectively, of the description. From the data listed in rows 1 and 2 of Table 8 and rows 1 and 3 of Table 10, a person of ordinary skills in the art would find obvious that the anti-inflammatory activity of emu oil in these examples was higher than the corresponding activity of the yellow fraction.

The description does not disclose any information about the residue resulting from the extraction of the yellow fraction.

Consequently, it can be stated that there is no known solution in the state of the art for the specific technical problem solved by the present invention.

DESCRIPTION OF THE INVENTION

Figure 1:
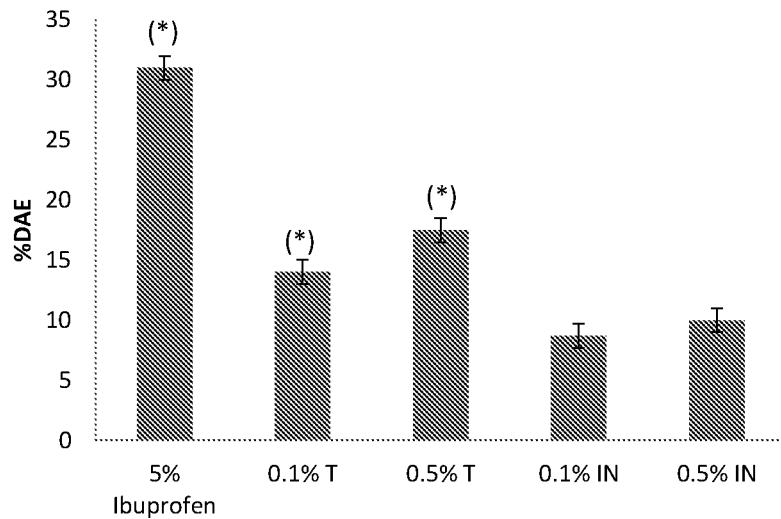
FIG. 1: The figure shows the dermal anti-inflammatory effect (DAE). Each bar represents the average and standard error of the % DAE obtained with each treatment applied to the right ear before the inflammatory stimulus produced by arachidonic acid (AA). n=4, *p<0.05 for Student's t. In vivo anti-inflammatory activity of the distillate is shown to be higher than the anti-inflammatory activity of emu oil.

The present invention relates to a molecular distillation process of refined emu oil.

More specifically, the present invention discloses a process for obtaining biologically active compositions from refined emu oil, wherein said process comprises the following steps:

a) feeding emu oil to a molecular distillation column comprising an evaporator to generate a distillate and a residue; and b) collecting the distillate from the column, the distillate being a biologically active composition, and c) collecting the residue from the column, the residue being a biologically active composition.

Surprisingly, the process allows obtaining two fractions having different activities and applications. On the one hand, the composition of the process distillate has an anti-inflammatory activity or effect with no regenerative effect, and the residue has a regenerative skin activity with no anti-inflammatory activity. Furthermore, in vitro and in vivo activity obtained in both cases is higher than the activity of the Emu oil itself. Regenerative activity would be important for skin burns while anti-inflammatory activity would be important for anti-irritant applications.

The high anti-inflammatory activity of the distillate makes it particularly useful for formulating anti-inflammatory or anti-irritant or protective pharmaceutical compositions against various skin damage causing agents for oral, injectable or topical use. Said compositions comprise the composition of a distillate from the process of the invention and one or more pharmaceutically acceptable excipients and/or additives, which, as a person skilled in the art knows, are excipients and/or additives characterized by being usually safe.

A pharmaceutical anti-inflammatory and anti-irritant composition for topical use, such as cream or gel, comprises, in addition to the distillate, the active ingredient, excipients and/or additives characterized by being usually safe, nontoxic, non-irritating under long-term exposure and with bandage, and preferably colorless and capable of transdermically delivering medicaments without producing a burning or tingling sensation. Said excipients and/or additives typically comprise, without limiting the invention, a lubricant, including but not limited to, glycerin; a preservative agent, including but not limited to, a dehydroacetic acid/benzyl alcohol/water mixture; a thickener or gelling agent, including but not limited to, carbapol, glyceryl stearate or cetyl alcohol; and a vehicle carrying the active ingredient or transdermal delivery agent, including but not limited to, triglycerides, an astringent agent, including but not limited to, various organic alcohols, and a neutralizing agent, including but not limited to, low percentage sodium hydroxide, in some cases, or triethylamine, in other cases. A typical anti-inflammatory or anti-irritant pharmaceutical composition for topical use is described in Example 2.

Furthermore, the skin regenerative or reparative activity of the distillation residue on skin burns makes it particularly useful for formulating skin burn creams.

In the present invention, the term "emu oil" comprises crude emu oil and/or refined emu oil.

Short-path or molecular distillation owes its name to the distance traveled by a steam stream before its condensation. In short-path distillation, the evaporator walls generate steam as the feed descends by gravity through the evaporator walls. The stream travels a "short distance" typically between 10 to 50 mm directly to the condenser in the evaporation chamber. Since the steam stream immediately condenses, the short-path distillation process prevents steam pressure rising, allowing operation at pressures as low as 0.0001 mbar. This in turn allows the purification of heat sensitive materials at lower temperatures, thus preventing their thermal degradation. Currently, the geometry of the distillation space of the molecular distillation units is a concave evaporation area formed by the inner face of an externally heated cylinder with the internal condenser operating at a temperature higher than the melting point of the distillate, close to the evaporator surface.

Distillation is called molecular distillation when the distance between evaporator and condenser in a short-path distillation apparatus is on the order of magnitude or less than the mean free path of the steam molecules at the operating conditions. However, the terms short-path distillation and molecular distillation are used interchangeably by the technical literature and by the present invention.

To carry out the invention, the emu oil is fed to a molecular distillation column at a rate between 1 kg/h*m$^2$ and 300 kg/h*m$^2$, preferably between 10 kg/h*m$^2$ and 200 kg/h*m$^2$. M$^2$ refer to the column evaporation surface area.

In one embodiment the evaporator temperature is between 160° C. and 250° C., preferably between 180° C. and 220° C. In one embodiment the column pressure is between 0.0001 mbar and 0.5 mbar, preferably between 0.001 mbar and 0.05 mbar. The distillate and residue leave separately from the column and are collected or taken from the column exit.

The distillation process results in a light fraction or distillate composition having an anti-inflammatory activity higher than the anti-inflammatory activity of the feed emu oil and a heavy fraction or residue composition having a skin regenerative or reparative activity on cutaneous burns higher than that of the feed emu oil.

EXAMPLES

Example 1

Emu Oil Distillation.

Emu oil was provided by the "Campos de la Unión" Emu Farm (San Carlos s/n•Casilla #339•La Unión•Los Rios Region•Chile) and meets the standards or technical certification requirements of the American Emu Association (AEA)

Emu oil was fed to a UIC KDL-5 molecular distillation unit with a mass feed flow of 11.8 kg/h*m$^2$. Other operating conditions were:

Evaporator temperature: 200° C.
Condenser temperature: 55° C.
Column pressure: 0.001 mbar
18.5 g of distillate and 451 g of residue were obtained from a total fed mass of 470 g.

Example 2

Emu Oil Distillation.

Emu oil was provided by the "Campos de la Unión" Emus Farm (San Carlos s/n•Casilla #339•La Unión•Los Rios Region•Chile) and meets the standards or technical certification requirements of the American Emu Association (AEA)

Emu oil was fed to a UIC KDL-5 molecular distillation unit with a mass feed flow of 11.8 kg/h*m$^2$. Other operating conditions were:

Evaporator temperature: 160° C.
Condenser temperature: 55° C.
Column pressure: 0.001 mbar
30 g of distillate and 270 g of residue were obtained from a total fed mass of 300 g.

Example 3

Composition of a Topical Anti-Inflammatory or Anti-Irritant Gel.

An anti-inflammatory or anti-irritant gel was prepared using part of the distillate of Example 1, its composition is shown in Table 1.

TABLE 1

Composition of an anti-inflammatory or anti-irritant gel.

| Ingredients | % by weight |
| --- | --- |
| Water | C.S.P. 100 |
| Glycerin | 3.00-8.00 |
| Denatured alcohol | 0.5-1.2 |
| 8% dehydroacetic acid/88% benzyl alcohol/ and 4% water mixture | 0.5-1.10 |
| Carbopol (gelling agent) | 0.50-1.00 |
| Perfume | 0.1-0.30 |
| Distillate of Example 1 | 0.10-1.00 |
| Sodium hydroxide | 0.03-0.05 |
| Total | 100.00 |

The gel may have a distillate percentage higher than that indicated in Table 1, adjusting accordingly the concentration of some of the other ingredients, such as water, for example.

The anti-inflammatory component of the gel is the distillate composition that acts, at the same time, to provide effective transport through the epidermis. However, the gel may comprise other additional compounds that contribute to said transport, including but not limited to, methyl, ethyl or isopropyl salicylate, isopropyl, butyl or amyl alcohol.

The function of the other components or additives in Table 1, all of them pharmaceutically acceptable, is evident for a person of ordinary skills in the art.

Example 4

In Vivo Anti-Inflammatory Activity of the Distillate of Example 1.

This protocol complies with the regulations of the ISP (Public Health Institute of Chile) Bioethics Committee and the procedures were carried out in accordance with the "Guide for the Care and Use of Laboratory Animals", published by the "National Institutes of Health (NIH-USA)".

Groups of 4 non-inbred, male, CF-1 mice, weighing between 20-25 g, were kept at 22±3° C. and humidity of 50-60%, artificial light/dark cycle of 12-12 hours and with conventional rodent feed ad libitum. Five minutes before applying 2 mg arachidonic acid (AA), each group was topically administered to the right ear a volume of 20 µL of 0.5 or 0.1% dilutions of an emu oil initial extract (IN) or a molecular distillation unit top fraction (T) in acetone p.a., or 5% ibuprofen as a positive control. 20 µL of acetone distributed in the same way was applied to the left ear. After 1 hour, the animals were humanely euthanized and a 6 mm diameter section of the left and right ear was pierced and weighed.

The dermal anti-inflammatory effect (DAE) was evaluated according to the following equation (% weight reduction):

$$\%DAE = \frac{Pc - Pt}{Pc} * 100$$

Where Pc of each animal is obtained from the weight difference in weight of the section (6 mm) of the right ear (treated with AA) minus the weight of the section of the left ear (treated only with AA and acetone). Pt corresponds to the weight difference between the right and left ear of the animals treated with the formulations or products under study.

All data are expressed as averages plus-minus standard error (±SEM). The statistical significance of the anti-inflammatory result with respect to AA was evaluated by means of a Student's t-test considering a p<0.05.

FIG. 1 shows the dermal anti-inflammatory effect (DAE). Each bar represents the average and standard error of % DAE obtained with each treatment applied to the right ear, before the inflammatory stimulus produced by arachidonic acid (AA). n=4, *p<0.05 for Student's t.

It can be seen that in vivo anti-inflammatory activity of distillate is higher than anti-inflammatory activity of emu oil (see FIG. 1).

Example 5

In Vitro Anti-Inflammatory Activity of the Distillate of Example 1.

The murine macrophage line Raw 246.7 was seeded at a concentration of 5×10$^5$ cell/mL in 48-well plates and maintained at 37° C. and 5% $CO_2$ in RPMI medium supplemented with 10% fetal bovine serum, penicillin-streptomycin and L-glutamine, adjusting to 1 mL as the final volume. Four hours later the cultures were washed with phosphate buffered saline and stimulated 24 h later with 1 µg/mL of lipopolysaccharide (LPS) in the absence or presence of a 0.1% dilution of emu oil input (IN-LPS) or top distillation fraction (T-LPS) or distillation residue fraction (R-LPS) in dimethylsulfoxide (DMSO) or an anti-inflammatory positive control composed of 1 µM dexamethasone (Dx-LPS). Culture supernatants were then collected and interleukin 6 (IL-6) concentration was evaluated as a parameter of inflammatory response by enzyme-linked immunosorbent assay (ELISA). 96-well plates were incubated with the primary antibody anti-IL-6 for 12 hours at 4° C. in carbonate buffer, pH 9.5. Then, 50 µL of each supernatant sample were incubated for 2 hours. The well was washed and incubated for 1 hour with a secondary antibody. Finally, the absorption of each well was measured at 650 nm in an ELISA plate reader. IL-6 concentration was calculated according to a reference curve made with a mouse IL-6 standard.

Figure 2:
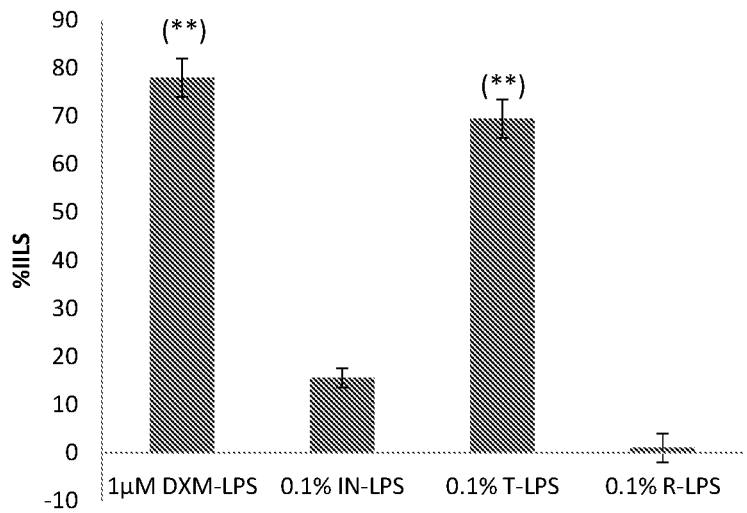
FIG. 2. The figure shows the percentage of inhibition of IL-6 secretion (% IILS) and its standard error under inflammatory stimulation with lipopolysaccharide (LPS, 1 µg/mL) together with 1 µM dexamethasone (DXM-LPS), or with 0.1% feed emu oil of Example 1 (IN-LPS), with 0.1% of the distillate of Example 1 (T-LPS) or with 0.1% of the residue of Example 1 (R-LPS). n=3, **p<0.01 for one-way Anova.

FIG. 2 shows the % inhibition of IL-6 secretion (IILS) as a measure of anti-inflammatory activity against LPS stimulation on cultured macrophage cells, according to the following equation:

$$\%IILS = \frac{ILin - ILf}{ILin}$$

wherein ILin and ILf correspond to the concentration of IL-6 detected in the culture treated with LPS and with LPS and the anti-inflammatory compound, respectively (IN-LPS, T-LPS and DXM-LPS)

It can be seen that in vitro anti-inflammatory activity of the distillate is considerably higher than anti-inflammatory activity of emu oil, while anti-inflammatory activity of the residue is inactive (see FIG. 2).

Example 6

Composition of a Regenerative Cream for Skin Burns.

TABLE 2

Composition of a regenerative cream for skin burns.

| Ingredientes | % by weight |
| --- | --- |
| water | C.S.P.100 |
| Glycerin | 1.0-10.0 |
| Cetostearyl alcohol/cetearyl glycoside | 0.5-3.0 |
| Glyceryl Stearate | 1.0-5.0 |
| Cetyl alcohol | 1.0-5.0 |
| Sorbitan monostearate | 0.5-1.0 |
| 8% dehydroacetic acid/88% benzyl alcohol/4% water | 0.5-1.0 |
| Capric and caprylic acid triglyceride | 1.0-2.0 |
| Residue obtained from Example 1 | 0.1-10.0 |
| Sodium stearoyl glutamate | 0.1-1.0 |
| Tocopheryl acetate | 0.1-0.5 |
| Glyceril caprylate | 0.1-0.5 |
| Sodium phytate | 0.05-0.2 |
| Total | 100.00 |

The gel may have a distillate percentage higher than that indicated in Table 1, adjusting accordingly the concentration of some of the other ingredients, such as water, for example.

The active principle of the formulation is the residue obtained from Example 1. The function of the other components or additives in Table 2, all of them pharmaceutically acceptable, is evident for a person of ordinary skills in the art.

Example 7

Regenerative Activity of the Residue.

This protocol has been carried out based on the recommendations of the OEDC Guideline TG402 (2017) and the ISO 10993-10: 2002 standard.

Healthy, young, albino, adult, male and female Sprague-Dawley rats having a body weight between 190-250 g were used. Animals were kept in a room at controlled temperature (22±3° C.) and humidity (50-60%), under an artificial light/dark cycle of 12-12 hours. The feed consisted of conventional rodent standard pellets and water ad libitum.

Animals were intraperitoneallly anesthetized with Ketamine+Xylasine (according to ULAM: Guidelines for Anesthesia and Analgesia of Rats, University of Michigan, 2005), a 20 $cm^2$ area on the back was then shaved, and a burn of approximately 2 cm in diameter was made using a metallic device at a temperature of 85 to 90° C., which was kept in contact with the skin for 2 seconds. Twenty-four hours later, daily doses of 1 mL of each of the formulations were administered, applied uniformly onto the exposed area of the skin (10% of the total area of the animal's body surface), ensuring to cover the entire wound. The effect of the product on day 15 was evaluated by measuring wound diameter reduction.

Each treatment group was composed by of 3 males and 3 females. 5% v/v, 1% v/v and 0.1% v/v concentrations of the residue from Example 1 in petrolatum were evaluated. In addition, a petrolatum blank and 5% v/v emu oil in petrolatum were used.

Figure 3:
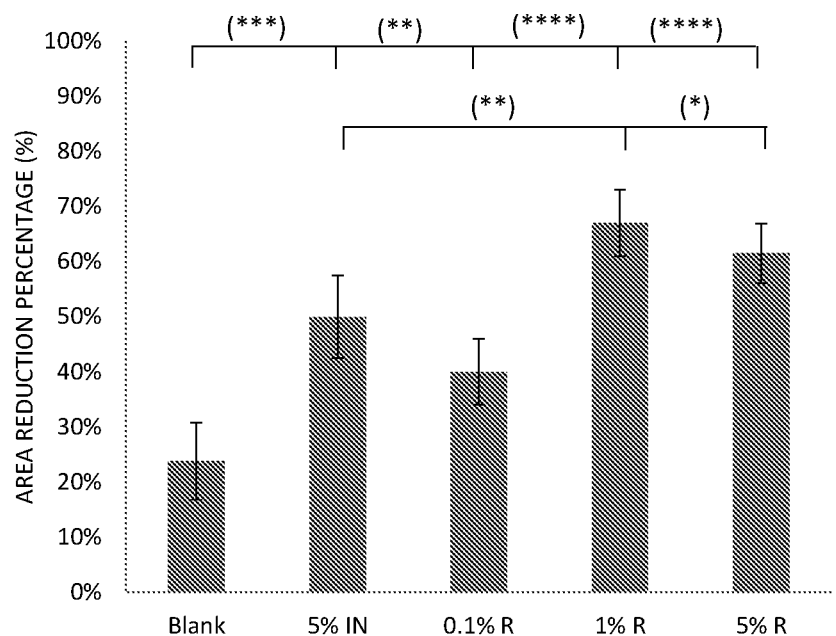
FIG. 3. Percentage reduction of burn wound size in the back of rats and their standard deviation, produced by treatment with petrolatum the vehicle (Blank) or the residue (R) of Example 1 at concentrations of 0.1, 1 and 5% or the feed oil of Example 1 (IN) at 5%. n=6. *p<0.05, p<0.01, *p<0.001 and ****p<0.0001 Student's t for Anova, according to Table 3.

FIG. 3 shows wound size percentage reduction and its standard deviation produced by treating burn wounds on rat backs with petrolatum vehicle (blank) or with concentrations of 0.1, 1 and 5% of the residue (R) of example 1, or 5% of the feed oil of example 1 (IN). n=6. *$p<0.05$, $p<0.01$, *$p<0.001$ and ****$p<0.0001$ by Student's t for Anova, according to Table 3.

TABLE 3

Significant p-values obtained according to the statistic analyzed by Student's t-test for Anova.

| Compared groups | Values |
| --- | --- |
| Blank/0.1% R | $1.7 \times 10^{-3}$ |
| Blank/1% R | $6.8 \times 10^{-7}$ |
| Blank/5% R | $2.5 \times 10^{-6}$ |
| Blank/5% IN | $1.8 \times 10^{-4}$ |
| 5% IN/5% R | $1.0 \times 10^{-2}$ |
| 5% IN/1% R | $1.2 \times 10^{-3}$ |
| 1% R/0.1% R | $1.6 \times 10^{-5}$ |

It can be seen that the residue from the 1% distillation is 30% more effective than the 5% emu oil (see FIG. 3).

The invention is a novel solution for obtaining biologically active compositions from emu oil.

The state of the art discloses obtaining a biologically active fraction or composition from emu oil, which is obtained by means of an oil chromatographic process using solvents such as hexane, dichloromethane, methanol and mixtures of dichloromethane and methanol. Said solvents must be recovered and recirculated to the process, which increases operating costs. The recovery of dichloromethane must be especially exhaustive since it is highly harmful if ingested or absorbed by the skin and its concentration for human use or consumption products is subject to strict regulations.

The process disclosed by the prior art leads to a biologically active composition, wherein said composition has an in vivo anti-inflammatory activity lower than the anti-inflammatory activity of emu oil.

The process of the present invention provides biologically active compositions produced by molecular distillation of the emu oil, organic solvent is not used, and not one, but two biologically active compositions are produced, one distillate having an in vivo anti-inflammatory activity higher than that of emu oil, and a distillation residue having a skin regenerative activity on cutaneous burns higher than that of emu oil.

The invention claimed is:

1. A process for obtaining biologically active compositions from refined emu oil comprising:
   a. feeding emu oil at a flow of between 1 to 300 kg/h*$m^2$ to a molecular distillation column at a pressure between 0.0001 mbar and 0.05 mbar and at an evaporator temperature between 160° C. and 250° C., to generate a distillate and a residue;
   b. collecting a distillate from the column, wherein the distillate is a first biologically active composition; and
   c. collecting a residue from the column, wherein the residue is a second biologically active composition.

2. The process according to claim 1, wherein the column feed flow in step a) is in the range of 10 to 200 kg/h*$m^2$.

3. The process according to, claim 1, wherein the column comprises a pressure between 0.001 mbar and 0.05 mbar and the evaporator temperature comprises a temperature between 180° C. and 220° C.

* * * * *